(12) United States Patent
Kolthammer et al.

(10) Patent No.: US 8,824,757 B2
(45) Date of Patent: Sep. 2, 2014

(54) METHOD AND APPARATUS FOR USING TIME OF FLIGHT INFORMATION TO DETECT AND CORRECT FOR MOTION IN IMAGING SCANS

(75) Inventors: Jeffrey Kolthammer, Cleveland Heights, OH (US); Patrick Olivier, Solon, OH (US); Piotr J. Maniawski, Chagrin Falls, OH (US)

(73) Assignee: Koninklijke Philips N.V., Eindhoven (NL)

( * ) Notice: Subject to any disclaimer, the term of this patent is extended or adjusted under 35 U.S.C. 154(b) by 208 days.

(21) Appl. No.: 13/509,656

(22) PCT Filed: Nov. 17, 2010

(86) PCT No.: PCT/IB2010/055248
§ 371 (c)(1),
(2), (4) Date: May 14, 2012

(87) PCT Pub. No.: WO2011/070465
PCT Pub. Date: Jun. 16, 2011

(65) Prior Publication Data
US 2012/0275657 A1 Nov. 1, 2012

Related U.S. Application Data

(60) Provisional application No. 61/285,205, filed on Dec. 10, 2009.

(51) Int. Cl.
*G06K 9/00* (2006.01)
*A61B 6/00* (2006.01)
*A61B 6/03* (2006.01)

(52) U.S. Cl.
CPC .............. *A61B 6/032* (2013.01); *A61B 6/5217* (2013.01); *A61B 6/541* (2013.01); *A61B 6/037* (2013.01)

USPC .......................................... 382/128; 382/107

(58) Field of Classification Search
None
See application file for complete search history.

(56) References Cited

U.S. PATENT DOCUMENTS

2009/0003655 A1* 1/2009 Wollenweber ................ 382/107

FOREIGN PATENT DOCUMENTS

WO 2007100955 A2 9/2007
WO 2009013661 A2 1/2009

OTHER PUBLICATIONS

Fayad, H.; Pan, T.; Roux, C.; Le Rest, C.C.; Pradier, O.; Clement, J.F.; Visvikis, D., "A patient specific respiratory model based on 4D CT data and a time of flight camera (TOF)," Nuclear Science Symposium Conference Record (NSS/MIC), 2009 IEEE , vol., No., pp. 2594,2598, Oct. 24, 2009-Nov. 1 2009.*
Ambwani, Sonal et al., A feasibility study of joint respiratory and cardiac motion correction for coronary PET/CT imaging, ISBI 2009, pp. 935-938.
Buehrer, M. et al., Prospective self-gating for simultaneous compensation of cardiac and respiratory motion, Magnetic Resonance in Medicine, vol. 60, Issue 3, Sep. 2008, pp. 683-690.

(Continued)

*Primary Examiner* — Nirav G Patel

(57) ABSTRACT

In accordance with one aspect of the invention a method and apparatus for utilizing time of flight information to detect motion during a medical imaging acquisition, such as a PET imaging acquisition, is provided. In accordance with another aspect of the invention, a method and apparatus for detecting and correcting for respiratory motion and cardiac motion in medical images, such as PET images, is provided.

35 Claims, 8 Drawing Sheets

(56) References Cited

OTHER PUBLICATIONS

Butner, Florian et al., List mode-driven cardiac and respiratory gating in PET, The Journal of Nuclear Medicine, May 2009, vol. 50, No. 5, pp. 674-681.

Dawood, Mohammad et al., Respiratory motion correction in 3-D PET data with advanced optical flow algorithms, IEEE Transactions on Medical Imaging, vol. 27, No. 8, Aug. 2008, pp. 1164-1175.

Falie, D., et al.; Statistical Algorithm for Detection and screening Sleep Apnea; 2009; IEEE Trans. on Signals, Circuits and Systems; pp. 1-4.

Kovalski, G., et al.; Dual "motion-frozen heart" combining respiration and contraction compensation in clinical myocardial perfusion SPECT imaging; 2009; J. Nuclear Cardiology; 16(3)abstract.

Kesner, A. L., et al.; Respiratory Gated PET Derived in a Fully automated Manner From Raw PET Data; 2009; IEEE Trans. on Nuclear Science; 56(3)677-686.

Klein, G. J., et al.; Fine-Scale Motion Detection Using Intrinsic List Mode PET Information; 2001; Mathematical Methods in Biomedical Image Analysis; pp. 71-78.

Lamare, F. et al., Correction of respiratory motion in dual gated cardiac imaging in PET/CT, 2008 IEEE Nuclear Science Symposium Conference Record, pp. 5264-5269.

Penne, Jochen et al., Robust real-time 3D respiratory motion detection using time-of-flight cameras, International Journal of CARS (2008) vol. 3, pp. 427-431.

Rahmim, Arman, Advanced motion correction methods in PET, Iran Journal of Nuclear Medicine 2005; vol. 13, No. 24, pp. 1-17.

* cited by examiner

METHOD AND APPARATUS FOR USING TIME OF FLIGHT INFORMATION TO DETECT AND CORRECT FOR MOTION IN IMAGING SCANS

CROSS REFERENCE TO RELATED APPLICATIONS

This application claims the benefit of U.S. provisional application Ser. No. 61/285,205 filed Dec. 10, 2009, which is incorporated herein by reference.

DESCRIPTION

The present application relates generally to the imaging arts. More specifically, it provides methods and apparatuses for using time of flight information to detect motion which occurs during a medical imaging acquisition, such as a positron emission tomography (PET) imaging acquisition. The present application also provides methods and apparatuses for correcting for respiratory and cardiac motion in PET images. The application subject matter finds use at least with PET imaging, and will be described with particular reference thereto. However, it also has more general application with other imaging methods and in other arts, such as SPECT imaging or CT imaging.

Motion that occurs during a medical imaging acquisition can be problematic, as it can result in the deterioration of image quality and compromise the clinical utility of the resulting image data. Motion artifacts can result from a variety of different kinds of motion, such as for example respiratory motion, cardiac motion, and gross patient motion. Respiratory motion is motion caused by the expansion and contraction of the lungs during a respiratory cycle. Cardiac motion is motion caused by the expansion and contraction of the heart during a cardiac cycle. Gross patient motion is motion caused by voluntary or involuntary muscular movement of body parts, such as the chest, arms or legs. The likelihood that any of these kinds of motion will be problematic can be increased during PET imaging acquisitions, because PET imaging acquisition times are typically lengthy, on the order of minutes or tens of minutes.

It is desirable to provide a method and apparatus for the detection of motion during a PET imaging acquisition using time of flight information. In addition, it is also desirable to provide a method and apparatus for defecting and correcting for respiratory motion and cardiac motion in PET images.

Aspects of the present invention address these matters, and others. According to one aspect of the present invention, a method and apparatus are provided for detecting motion during a PET imaging acquisition using time of flight information.

According to another aspect of the present invention, a method and apparatus are provided for detecting and correcting for respiratory motion and cardiac motion in PET images.

Still further aspects of the present invention will be appreciated by those of ordinary skill in the art upon reading and understanding the following detailed description. Numerous additional advantages and benefits will become apparent to those of ordinary skill in the art upon reading the following detailed description of preferred embodiments.

The invention may take form in various components and arrangements of components, and in various process operations and method steps and arrangements of process operations and method steps. The drawings are only for the purpose of illustrating preferred embodiments and are not to be construed as limiting the invention.

I. Time of Flight PET Technology

Figure 1:
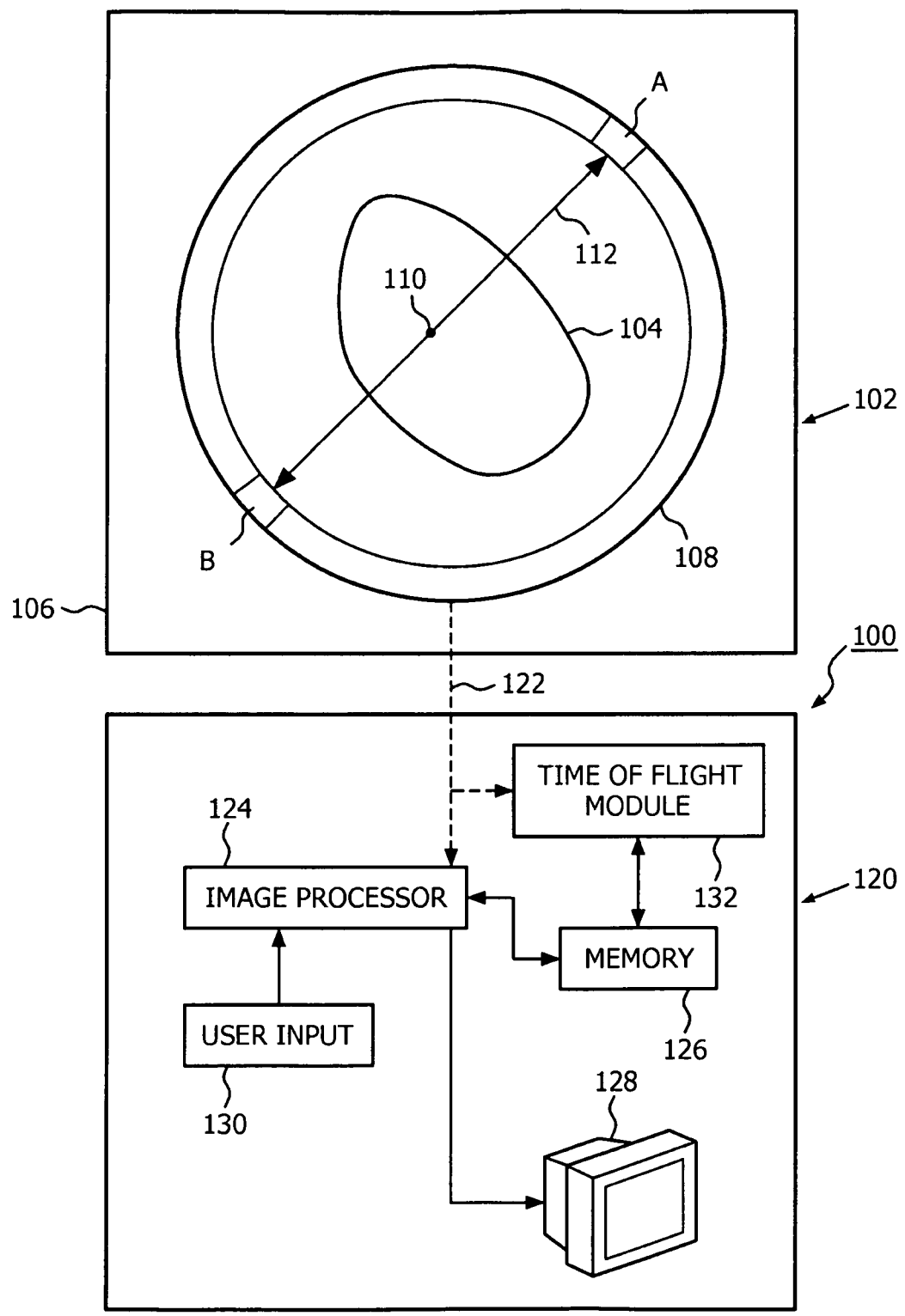
FIG. 1 is a schematic view of an exemplary PET imaging system.

An exemplary time of flight PET imaging system 100 is illustrated schematically in FIG. 1. The time of flight PET imaging system 100 includes a PET imaging scanner 102. A patient or an imaged subject 104 is placed within a gantry 106 of the PET imaging scanner 102. The gantry 106 of the illustrated embodiment of the PET imaging system 100 contains several photon detectors disposed in a ring 108 around the patient 104 to detect coincident photon pairs emitted by positron—electron annihilations 110. Two such detectors A and B are shown in FIG. 1. In an actual PET imaging scanner 102, a detector ring 108 will typically have several detectors, and also there may typically be many detector rings set side by side. For the sake of simplicity, FIG. 1 illustrates a 2-dimensional system. However, the concepts being illustrated apply equally well to a 3-dimensional system. In additional embodiments of the PET imaging system 100, the gantry may contain detectors that are not arranged in a ring geometry, such as two opposing plate detectors.

To obtain a PET image of a subject 104, a radiopharmaceutical is first injected into the subject 104. The radiopharmaceutical contains a targeting aspect which interacts with a molecule or process of interest within the patient's body, such as glucose metabolism. The radiopharmaceutical also contains a positron-emitting radionuclide. An emitted positron will collide with an electron from a nearby atom, and the positron and the electron annihilate. As a result of the annihilation, two different photons are emitted in substantially opposite directions along a line of response 112. The photons both travel at the same speed, the speed of light indexed for the medium they are passing through. The ring 108 of detectors record these photons, along with PET imaging data associated with the photons such as the time each photon is detected.

The PET imaging scanner 102 passes the PET imaging data recorded by the ring 108 of detectors, such as detectors A and B, on to a PET imaging, processing and display system 120 through a communication link 122. Although the PET imaging scanner 102 and the PET imaging, processing and display system 120 are shown and described here as being separate systems for purposes of illustration, they may in other embodiments be part of a single, unitary system. The PET imaging data passes to an image processor 124 which stores the data in a memory 126. The image processor 124 electronically processes the PET imaging data to generate images of the imaged patient or other object 104. The image processor 124 can show the resulting images on an associated display 128. A user input 130 such as a keyboard and/or mouse device may be provided for a user to control the processor 124.

A given detector, such as the detector A, including associated electronics, is able to very accurately identify the time at which it detects a photon. If two detectors such as the detectors A and B in FIG. 1 each record receipt of a photon within a given coincidence time period, it is assumed that the pair of photons resulted from a positron—electron annihilation event such as 110. In particular, it is assumed that the annihilation 110 occurred somewhere along the straight line connecting the detectors A and B, called the line of response 112 as shown in FIG. 1. Such pairs of detection events, or "coincidences," are recorded by the PET imaging scanner 102. Using image reconstruction algorithms executed by the image processor 124, the time of flight PET imaging system 100 can use such coincidence events to determine the distribution of the radiopharmaceutical in the patient. That distribution is used to generate a PET image.

In time-of-flight PET imaging, a coincidence event is acquired by two detectors such as A and B along with the difference in arrival time of the two coincident photons. Because the two coincident photons both travel at substantially the same speed, the arrival time difference has a direct correlation to the time of flight of the photons from the annihilation point 110 to the coincident detectors A and B. Because of that, the system 120 can approximately calculate the position along the line of response 112 where the annihilation 110 occurred, increasing the resolution of the PET image reconstruction. Thus a time of flight module 132 may be employed for this and other purposes. As illustrated in FIG. 1, the time of flight module 132 is located within the PET imaging, processing and display system 120. In various, additional embodiments the time of flight module 132 may be located within the PET imaging scanner 102 or can be located remotely from the PET imaging system 100. The time of flight module 132 may be implemented in hardware or software.

II. Use of Time of Flight Information to Detect Motion During an Imaging Acquisition One aspect of the present invention is directed generally to a method and apparatus for using time of flight information to detect motion, such as gross patient motion and/or respiratory motion, during an imaging acquisition. Thus this aspect of the present invention is particularly useful in a PET imaging acquisition, but in its broader aspects it may be used in connection with other kinds of imaging acquisitions. The exemplary method and apparatus provided herein may be used to detect motion during an image acquisition without requiring the use of an external device and without analyzing reconstructed image data, although it may also be used in conjunction with such methods.

In the past gross patient motion has typically been addressed by repeating multiple imaging acquisitions, or by re-processing a single set of imaging acquisition data. The former technique often leads to increased radiation exposure to both the subject and clinical staff, and the latter technique increases the required image processing time. Accordingly, it is desired to provide an apparatus and method for detecting gross patient motion during a medical imaging acquisition, in near real-time, thus reducing the need for repeating the imaging procedure to improve the clinical image quality. If gross patient motion is detected during an imaging procedure, it can be addressed at that time as opposed to waiting until after the imaging acquisition is completed to detect the gross motion.

With respect to respiratory motion, although its magnitude is typically small in comparison to gross patient motion, still the time-averaging of data over many respiratory cycles can spatially degrade images in areas most affected by such motion. In the past motion transducers such as bellow transducers have been utilized to measure the physical motion of the chest or abdomen during data acquisition. The information obtained from such motion transducers is then used in respiratory gating in an effort to compensate for the respiratory motion of the patient. Additional methods such as use of video cameras have also been applied to monitor respiratory motion and obtain information for respiratory gating. However, such methods require use of expensive equipment and the clinical utility of the imaging data produced using such equipment is not optimal.

Accordingly, it is desired to provide an apparatus and method for detecting and characterizing respiratory motion without the need for external transducers, video cameras, or other such equipment. The elimination of such equipment can reduce the overall cost of the system, the procedure or clinical cost, as well as the complexity and likelihood of errors in time-based or amplitude-based respiratory gating.

Figure 2:
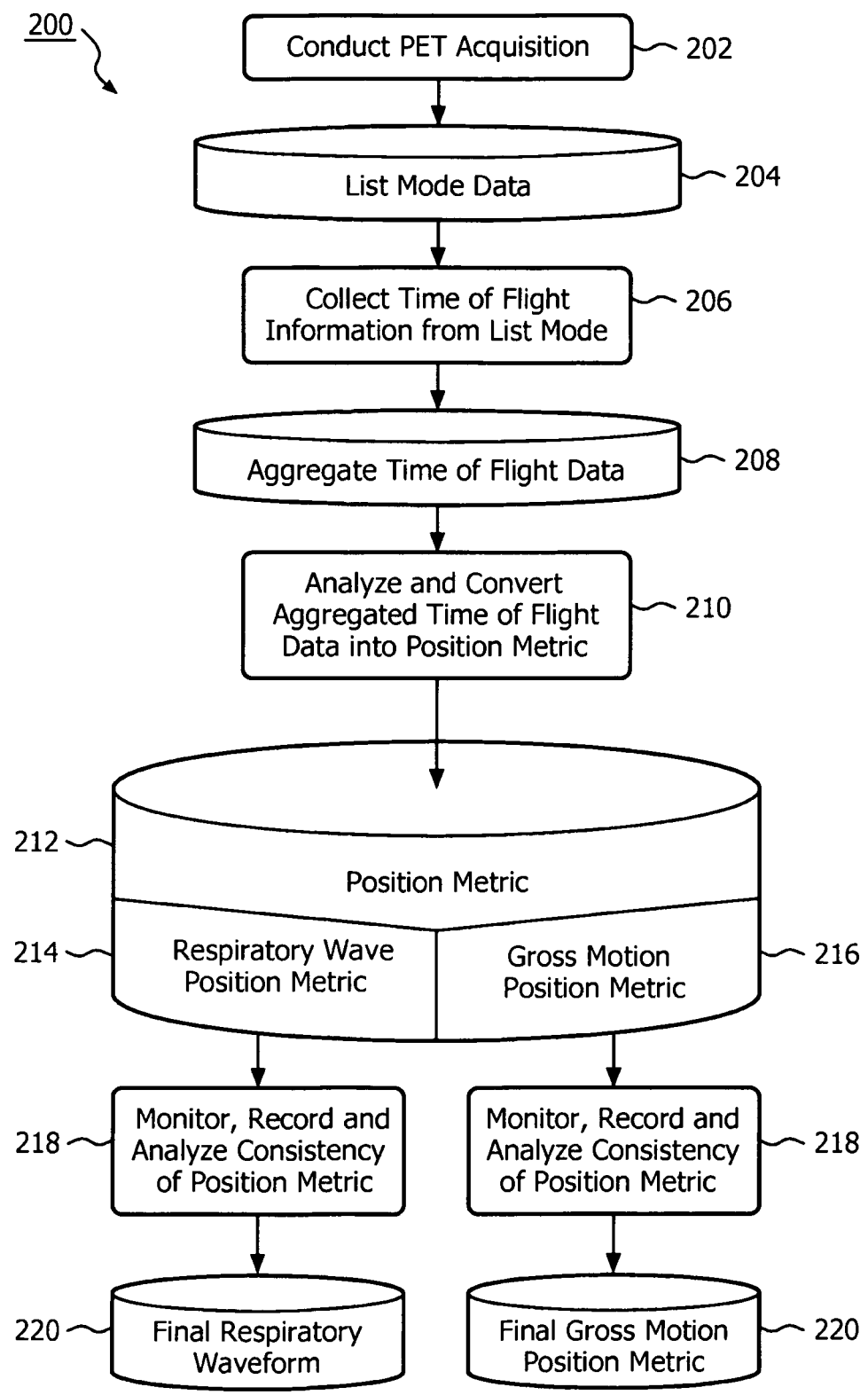
FIG. 2 depicts an exemplary method for detecting motion using time of flight information.

An exemplary motion detecting method 200 according to one aspect of the present invention is illustrated in FIG. 2. The exemplary method 200 utilizes time of flight information to detect gross patient motion and/or respiratory motion during an imaging procedure.

In step 202, a PET imaging system such as the system 100 is utilized to detect photon coincidence events and collect related imaging data concerning such coincidences, such as the time of flight of the coincidence. Such imaging data may be stored in a list mode 204 in memory 128. In various embodiments, the list mode 204 contains all of the imaging data from an entire imaging procedure. In additional embodiments, the list mode 204 includes only a portion of the total imaging data corresponding to a time segment of the imaging procedure and the storage of the imaging data may be an ongoing process so that the imaging data from a portion of the imaging procedure is being analyzed and/or manipulated as additional data is being collected (i.e., a transient process). Based on the time of flight information in the data 204, the approximate location of the annihilation 110 within the gantry 106 can be determined and added to the data 204. This may be done in pseudo-continuous space, where each photon coincidence event is localized to a bin along a line of response 112, wherein the bins may represent for example 5 mm intervals.

In step 206, the time of flight differences from the list mode data 204 are collected or aggregated to generate aggregate time of flight data 208. As mentioned above with respect to the list mode 204, the time of flight data 208 can be generated for the entire imaging procedure or can be separately generated for portions of the imaging procedure in a transient process. The aggregated time of flight data 208 is simply a selection from the overall list mode data 204 which is large enough to provide a reliable sample of data. Referring again to FIG. 1, the aggregate time of flight data 208 may for example be generated by a time of flight module 132. For example, the aggregate time of flight data 208 may be compiled into a histogram. The aggregation 208 preferably comprises a few seconds of imaging time, on the order of millions of photon coincidence events, although any time duration which provides a meaningful data sample may be employed.

Optionally, the collection 206 and aggregation 208 of the list mode data 204 may be limited to a subset of the data 204 in which motion might be expected. For example, if the imaged subject 104 is disposed within the gantry 106 with his or her back or chest lying on a table, as is typical, then respiratory motion of the subject 104 will chiefly result in vertical motion of the subject's chest within the gantry 106. Thus, the collection 206 and aggregation 208 of the list mode data 204 may be limited to or weighted towards vertical lines of response 112 within the gantry 106.

Another typical example is where gross patient movement of the patient's arms or legs might be expected during the imaging scan. In that event, the collection 206 and aggregation 208 of the list mode data 204 may be limited or weighted to annihilation events occurring in extreme horizontal positions within the gantry 106.

In various further embodiments of the exemplary method 200, the collection 206 and aggregation 208 of list mode data 204 may be limited to a pair of detectors, such as detectors A and B in FIG. 1, or a limited set of such paired detectors. In yet additional embodiments, the data 204 that is collected 206 and aggregated 208 may be limited to a particular line of response 112 or a range of line of response 112 angles, such angles being relative to the ring 108 or axial angles. In yet additional embodiments, all of the gathered data 204 is collected 206 and aggregated 208.

In step 210, the aggregate time of flight data 208 is analyzed and converted into one or more position metrics 212. The position metric 212 reflects the movement of the time of flight data over the course of time, and therefore the movement of the imaged subject 104 over the course of time. This position metric 212 may be displayed to the operator of the PET imaging system 100 in or near real time.

As one example of the exemplary method 200, the aggregate time of flight data 208 is converted into a respiratory wave position metric 214. The respiratory wave position metric 214 may, for example, be averaged or reduced to a conventional respiratory wave to help in the detection of respiratory motion. To convert the aggregate time of flight data 208 into a respiratory wave position metric 214, an initial identification may be made of the maximum and minimum positions corresponding to the respiratory motion, based on an analysis of the aggregate time of flight data 208. For example, the anterior-posterior motion of the subject within selected imaging slices along the longitudinal or "z" axis of the imaged subject 104 may be monitored for a time period, such as five or ten seconds, to generate a signal related to the amplitude of respiratory motion. That amplitude data may then be used to correlate the aggregate time of flight data 208 with a conventional respiratory wave to generate the respiratory wave position metric 214. In various embodiments, the conventional respiratory wave may be a measured signal or a pre-generated archetype respiratory signal. Optionally, data processing or smoothing may be applied to the respiratory wave position metric 214 for optimization purposes.

Alternatively or in addition to the respiratory wave position metric 214, the aggregate time of flight data 208 may be converted into a gross motion position metric 216 in various embodiments. To convert the aggregate time of flight data 208 into a gross motion position metric 216, the aggregate time of flight data 208 is utilized to obtain information regarding the center of activity. The center of annihilation activity may for example be determined for the entire imaged subject 104 or for only a portion of the imaged subject. As yet another example, the gross motion position metric 216 may reflect the 2-dimensional center of photon annihilation activity within one or more axial slices of imaging data 204. Various combinations are also possible.

In step 218, the consistency of the position metric 212 is monitored, recorded and analyzed over time. The position metric is then used to generate a final position metric 220. If the position metric 212 is a respiratory wave position metric 214, it may be used to generate a final respiratory waveform 220 for use in image reconstruction. For example, the final respiratory waveform 220 can be used for respiratory gating or to otherwise classify the time sequence of the list mode data 204. In this manner, respiratory gating can be accomplished using the exemplary method 200 without the need for an external device, such as a bellows transducer or video camera. In various embodiments of the exemplary method 200, the final respiratory waveform 220 is used to generate gating signals that are inserted into the list mode data 204 to mark the list mode data for time-based respiratory framing. In additional embodiments, the final respiratory waveform 220 is utilized to generate a respiratory amplitude for use in flexible, amplitude based gating. Such respiratory gating may be used, for example, in radiation therapy planning. In yet further embodiments, the final respiratory waveform 220 may be analyzed in near real time during the imaging acquisition to determine whether the subject's respiratory motion is exceeding pre-set thresholds and, if it is, then send a warning signal to the imaging operator.

If the position metric, is a gross motion position metric, it may be used to generate a final gross motion position metric 220 for use in image reconstruction. If the position metric 212 is a gross motion position metric 216, it can be monitored in step 218 and compared to one or more pre-selected motion threshold(s) to alert the operator of the PET imaging system 100 that gross patient motion has occurred when a pre-selected motion threshold is exceeded. In various embodiments of the exemplary method 200, the warning that is provided to the operator of the PET imaging system 100 is accompanied with information about the region of the imaged subject 104 where gross motion is suspected to have occurred. In yet additional embodiments, information regarding the direction and/or magnitude of the gross motion is provided to the operator. This information regarding the suspected gross motion may be used to guide an interpretation of the reconstructed image, or as a basis to start imaging acquisition over again. In various embodiments of the exemplary method 200, gross motion time flags are introduced into the list mode data 204 for use in separating the image data into images prior to the gross motion and images after the gross motion, or other diagnostic purposes.

III. Correction of Respiratory Motion and Cardiac Motion in PET Images

As described previously, motion that occurs during a medical imaging acquisition can be problematic, as it can result in the deterioration of image quality and compromise the clinical utility of the resulting image data. Two particular sources of motion during medical imaging procedures are respiratory motion and cardiac motion. Both respiratory motion and cardiac motion degrade the quality of the resulting image and introduce motion artifacts.

In the past, attempts have been made to correct for both respiratory motion and cardiac motion in PET images, such as cardiac PET images, by dividing or gating the data into a series of cardiac gated windows. Cardiac gating has most commonly been performed using the aid of an electrocardiograph (ECG) device to correlate the gated windows with the cardiac cycle. As described previously, respiratory gating has most commonly been performed using respiratory information gathered by external devices, such as a bellows transducer, video cameras, or other equipment to correlate the gated windows to the respiratory cycle. The gated windows of the data are then reconstructed to form an image using mathematical algorithms, which provide for spatial registration of the reconstructed images.

It is desired to provide an apparatus and method for characterizing and removing both respiratory motion and cardiac motion from a medical image. One aspect of the present invention is directed generally to a method and apparatus for correcting respiratory motion and cardiac motion in PET images. The exemplary method and apparatus provided herein are useful for characterizing and correcting for both respiratory motion and cardiac motion without the need for an external device to gather information regarding the respiratory motion. The method may, however, in some embodiments be used in conjunction with such devices.

Figure 3:
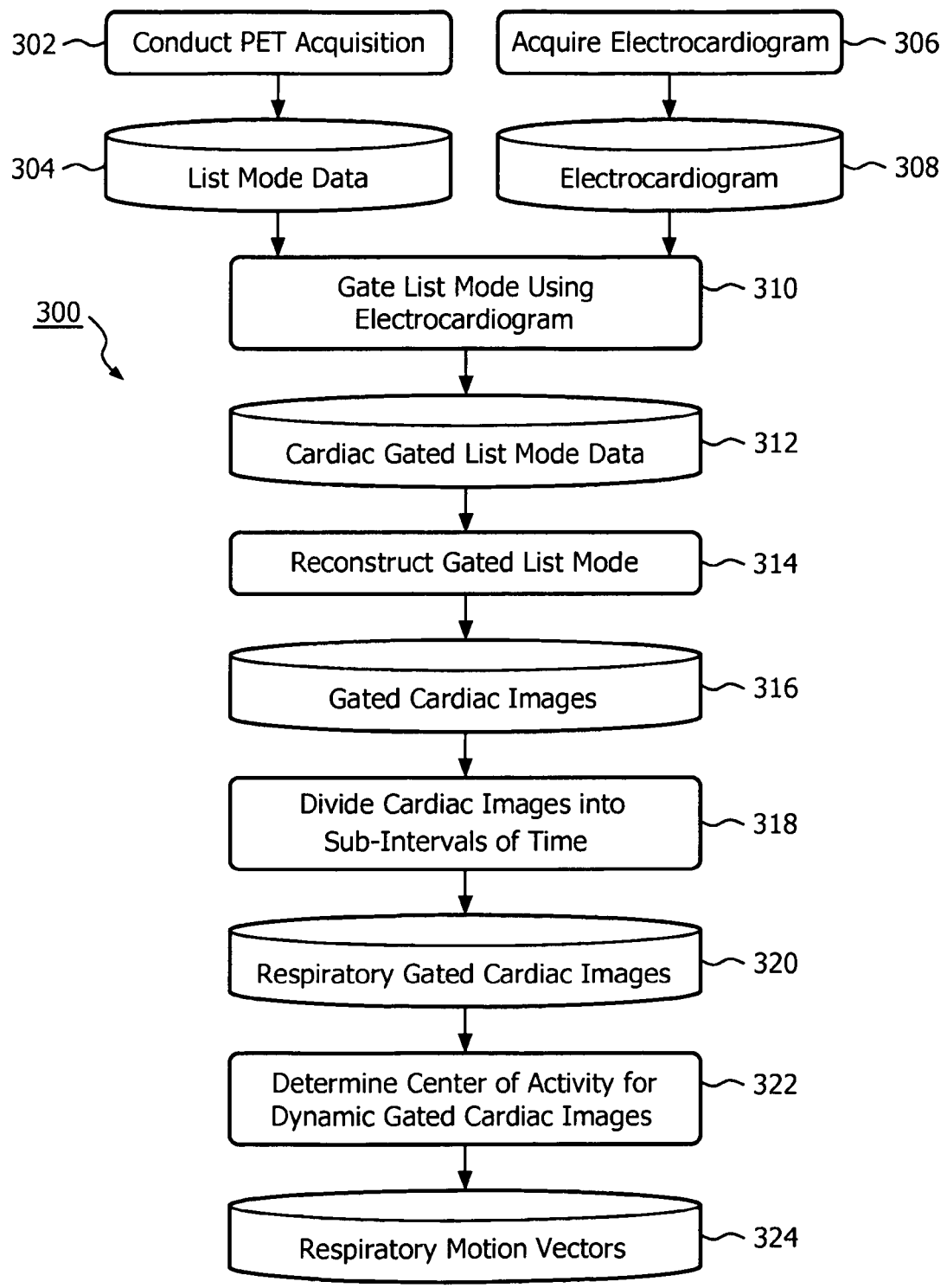
FIG. 3 depicts an exemplary motion characterization and correction method.

An exemplary motion characterization and correction method 300 according to one aspect of the present invention is illustrated in FIG. 3. The exemplary method 300 corrects for both respiratory motion and cardiac motion in cardiac PET images. Although the exemplary method 300 is directed to cardiac PET images, additional embodiments of the method are applicable to other types of PET imaging or other imaging modalities, such as CT or SPECT, or combined imaging modalities, such as PET/CT and SPECT/CT imaging.

In step 302, a PET imaging system such as the system 100 is utilized to conduct a cardiac PET acquisition and detect photon coincidences arising from annihilation events 110 occurring in the area of the heart of an imaged subject 104. The information from the cardiac PET acquisition is collected in a list mode data 304 that is stored in memory 128.

Figure 4:
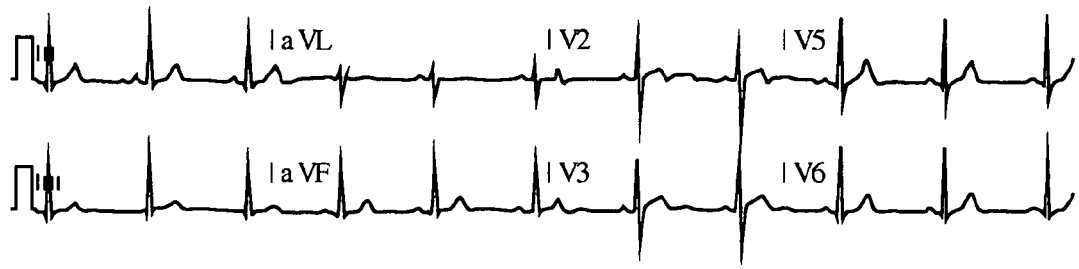
FIG. 4 depicts an exemplary electrocardiogram (ECG) signal recording.

In step 306, a digitized signal of the heart muscle contractions of the imaged subject 104 is acquired concurrently with the cardiac PET acquisition 302 in the form of an electrocardiogram (ECG) 308. An exemplary electrocardiogram (ECG) recording is set forth in FIG. 4. The horizontal axis of the ECG represents the passage of time, while the plotted curve reflects the electrical activity and therefore the phase of the subject's heart at any given point in time along that axis. Thus, for example, the ECG indicates the starting and stopping times of the cardiac cycle, as the heart repeatedly expands and contracts.

In step 310, the time-stamp of the electrocardiogram (ECG) 308 is synchronized with the acquired list mode data 304 to generate cardiac gated list mode data 312. More specifically, the acquired list mode data 304 is taken over the course of several heartbeats or cardiac cycles. The list mode data 304 contains the time at which each photon coincidence was detected. The electrocardiogram (ECG) 308, in turn, provides the phase of the patient's heart within the cardiac cycle at that particular point in time. The cardiac cycle may, as one example, be subdivided into a series of cardiac gated windows such as 8 to 16 windows. Then, based on the electrocardiogram (ECG) 308 data, each detected photon coincidence in the list mode data 304 is identified with a cardiac gated window of the cardiac cycle. Thus, the cardiac gated list mode data 312 for a particular gated window will have data corresponding only to the phase of the heart for that window, but taken during different repetitions of the cardiac cycle over the entire imaging acquisition time.

In step 314, the cardiac gated list mode data 312 in each of the cardiac gated windows is separately reconstructed to form an image of the heart. This produces a series of cardiac gated cardiac images 316, with each image corresponding to one of the gated windows of the entire cardiac cycle. So if the cardiac cycle was divided into 16 gated windows, then there will be 16 gated cardiac images 316.

Figure 5:
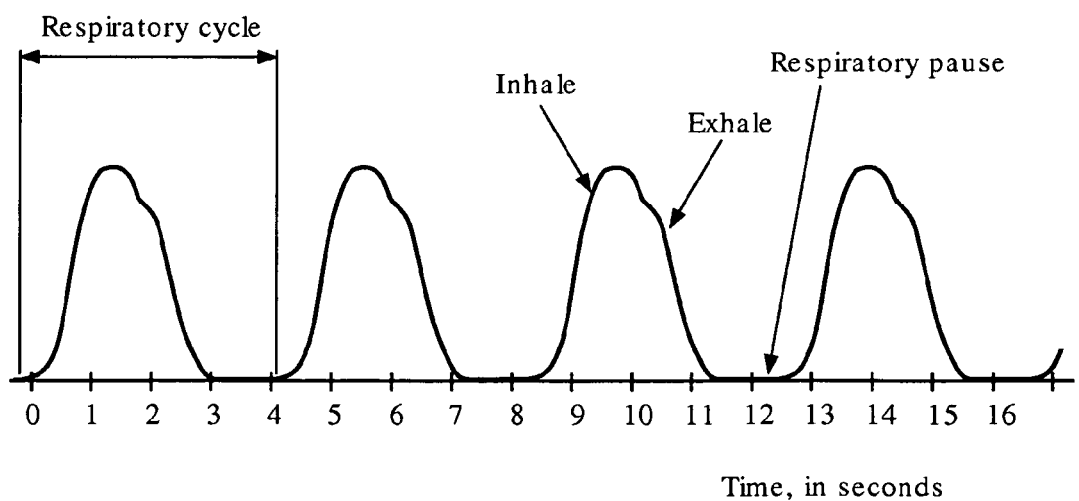
FIG. 5 is an exemplary respiratory waveform.

Now considering the respiratory cycle, because a typical PET acquisition usually lasts an extended period of time on the order of minutes or tens of minutes, it will contain data spanning multiple respiratory cycles. For example, if a particular cardiac PET acquisition lasts 5 minutes, and the length of time of an average respiratory cycle is around 4 seconds (as an example), the imaged subject 104 will go through about 75 respiratory cycles during the PET acquisition. An exemplary respiratory wave or respiratory cycle is depicted in FIG. 5. Each of the cardiac gated cardiac images 316 is blurred due to the motion of the heart caused by these respiratory cycles. In other words, the list mode data 304 photon coincidences are spread out in space due to the movement of the heart caused by the contraction and expansion of the subject's lungs. That respiratory movement can cause the imaged subject's heart to move up, down, left, right, forward, backward, or even be rotated through a torsional motion during the PET image acquisition. Accordingly, the blurring and motion artifacts introduced into the cardiac gated cardiac images 316 due to respiratory motion may advantageously be removed.

The number of cardiac gated windows for the cardiac cycle is chosen so that, within a particular gated window, one would expect very little or no movement of the heart. As a consequence, any movement of the annihilation data within each gated window most likely results from respiratory movement, not cardiac movement. In this way, respiratory motion of the heart can be isolated from cardiac motion, and may be approximated by movement of the heart within a particular cardiac gated window.

Thus, in order to extract the respiratory motion in step 318, each one of the cardiac gated windows defining the cardiac gated images 316 is further divided into sub-intervals of time. For each cardiac gated cardiac image 316 corresponding to a given gated window of the cardiac cycle, the list mode data 304 is assigned to the appropriate sub-interval within the cardiac gated window, again using the electrocardiogram (ECG) 308 as a guide. The list mode data 304 assigned to each of those sub-intervals represents a respiratory gated cardiac image 320. Any number of time sub-intervals may be used for this purpose.

As one example, assume the entire cardiac PET acquisition contains 150 million detected photon coincidences over a 5 minute acquisition time, and the gated list mode data 316 is divided into 20 gated windows. Then there will be about 7.5 million detected photon coincidences in each cardiac gated image 316 (150 million/20=7.5 million). Further suppose 0.1 second is the length of the time sub-interval used. Then, there will be a total of 3,000 respiratory gated cardiac images 320 within the entire list mode data set 304 (5×60/0.1=3,000). Or, there will be 150 respiratory gated cardiac images 320 within each of the 20 cardiac gated windows of the cardiac cycle (3000/20=150). Each of the 3,000 respiratory gated cardiac images 320 contains 2,500 detected photon coincidences (7.5 million/3,000=2,500).

In step 322, the center of activity is calculated for each of the respiratory gated cardiac images 320. As discussed above, any movement of that center of activity represents respiratory movement which has been isolated from cardiac movement. Therefore any difference(s) in the center of activities of the respiratory gated cardiac images within the same cardiac gated window is indicative of respiratory movement, not cardiac movement. In that way any such difference(s) may be used to generate respiratory motion vectors 324 which may be used to corrected the list mode data 204 for respiratory motion in image reconstruction.

Figure 6:
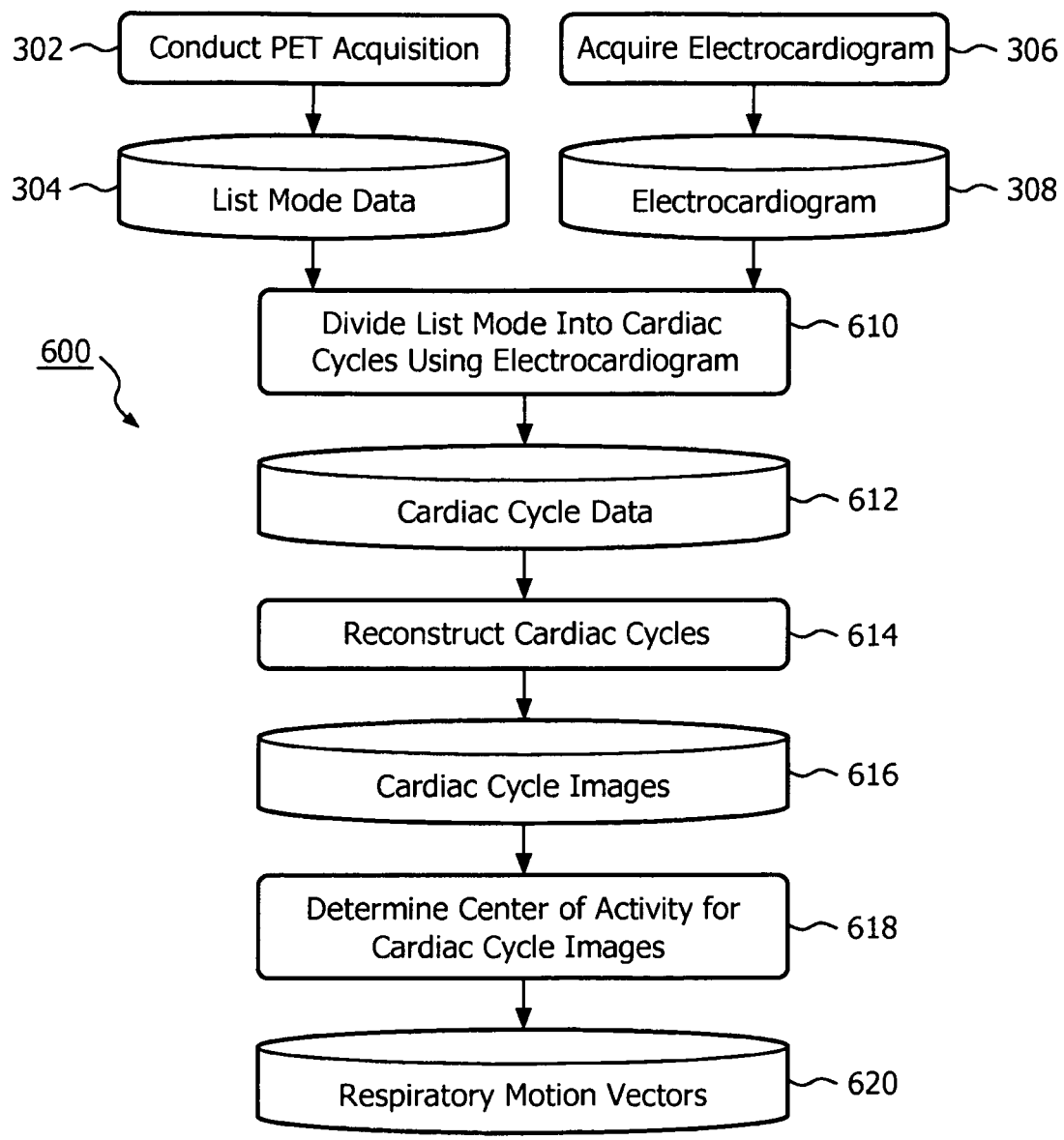
FIG. 6 depicts another exemplary motion characterization and correction method.

Referring now to FIG. 6, another exemplary method 600 for motion characterization and correction is illustrated. In step 302, a PET imaging system such as the system 100 is utilized to conduct a cardiac PET acquisition and detect photon coincidences arising from annihilation events 110 occurring in the area of the heart of an imaged subject 104. The information from the cardiac PET acquisition 302 is collected in a list mode data 304 that is stored in memory 128.

In step 306, a digitized signal of the heart muscle contractions of the imaged subject 104 is acquired concurrently with the cardiac PET acquisition 302 in the form of an electrocardiogram (ECG) 308. An exemplary electrocardiogram (ECG) recording is set forth in FIG. 4. The horizontal axis of the ECG represents the passage of time, while the plotted curve reflects the electrical activity and therefore the phase of the subject's heart at any given point in time along that axis. Thus, for example, the ECG indicates the starting and stopping times of the cardiac cycle, as the heart repeatedly expands and contracts.

In step 610, the time-stamp of the electrocardiogram (ECG) 308 is synchronized with the acquired list mode data 304 to generate cardiac cycle data 612. More specifically, the acquired list mode data 304 is taken over the course of several heartbeats or cardiac cycles. The list mode data 304 contains the time at which each photon coincidence was detected. The electrocardiogram (ECG) 308, in turn, identifies which of the heart beats—the first cycle, the second cycle, etc.—corresponds to that particular point in time. There may have been, as one example, 300 repetitions of the cardiac cycle during a five-minute imaging acquisition time. Then, based on the electrocardiogram (ECG) 308 data, each detected photon coincidence in the list mode data 304 is identified with a particular repetition of the cardiac cycle during the image acquisition period. Thus, the cardiac cycle data 612 for a particular repetition of the cardiac cycle contains data corresponding only to that repetition of the cardiac cycle.

In step 614, the cardiac cycle data 612 for each of the cardiac cycles is separately reconstructed to form an image of the heart. This produces a series of cardiac cycle images, with each image corresponding to one entire cardiac cycle.

In step 618, the center of annihilation activity for each of the cardiac cycle images 616 is calculated. The cardiac motion affects the position of the center of annihilation in a negligible way, because each image 616 corresponds to an entire cardiac cycle. Thus, any movement of the center of photon annihilation activity in these images, from image to image, results from respiratory movement and not cardiac movement. In this way, respiratory motion of the heart can be isolated from cardiac motion. Any difference(s) in the center of annihilation activity between cardiac cycle images 616 may be used to generate respiratory motion vectors 620 for use in correcting for respiratory motion in image reconstruction.

Each cardiac cycle image 616 contains a sufficient number of photon coincidence counts to calculate the center of activity for the particular cardiac cycle represented by the image 616. By way of example, a five minute PET acquisition will include approximately 300 cardiac cycles, assuming a 1 second cardiac cycle. If a particular five minute cardiac PET acquisition contains 150 million photon coincidence counts, for example, there will be 500,000 photon coincidence counts per cardiac cycle image 616 for that particular acquisition (150 million/300=500,000).

Both exemplary motion correction methods 300 and 600 estimate the same respiratory motion, occurring during the same PET acquisition, but they do so in different ways. Accordingly, respiratory motion vectors 324 obtained from the first exemplary method 300 and respiratory motion vectors 620 obtained from the second exemplary method 600 both represent estimates for the same respiratory motion.

Figure 7:
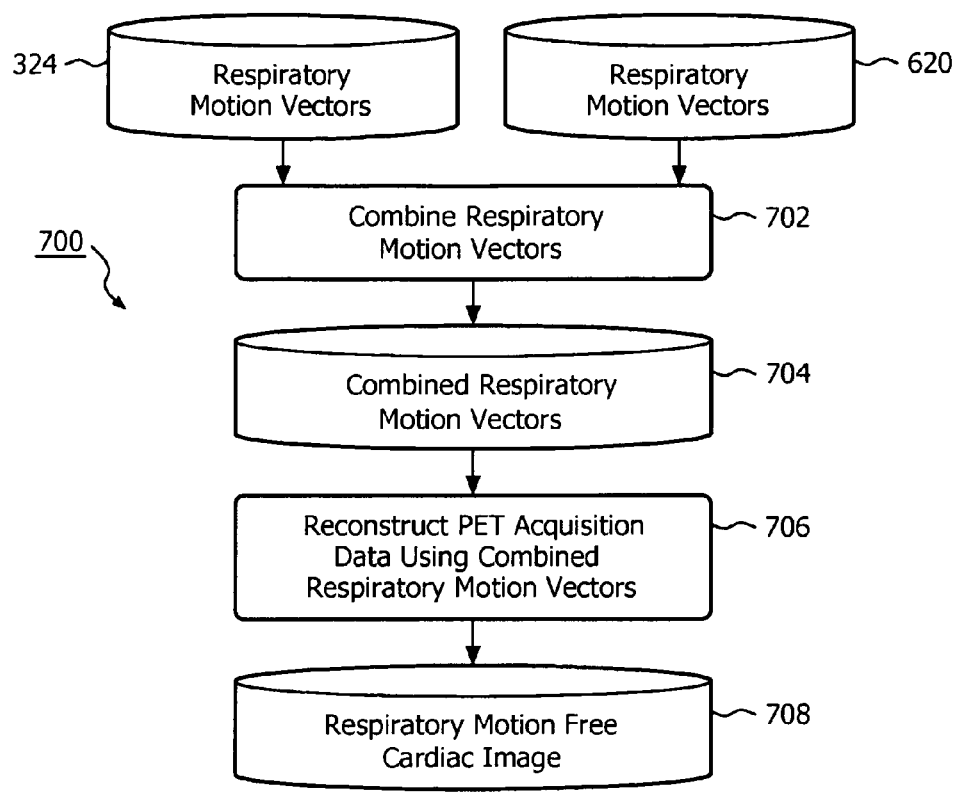
FIG. 7 depicts an exemplary method for combining the results of the methods of FIG. 3 and FIG. 6.

In some embodiments of the present invention, either exemplary motion correction method 300 or 600 may be individually used to correct for the respiratory motion. In additional embodiments, both respiratory motion vectors 324 and respiratory motion vectors 620 may be combined such as by averaging to generate combined respiratory motion vectors. Referring now to FIG. 7, an exemplary method 800 for combining the respiratory motion estimates from exemplary method 300 and exemplary method 600 is illustrated.

In step 702, the respiratory motion vectors 324 are combined with the respiratory motion vectors 620 to generate combined respiratory motion vectors 704. It is desirable to appropriately combine respiratory motion vectors 324 with respiratory motion vectors 620 to generate the most probable respiratory estimation. Respiratory motion vectors 324 can be combined with respiratory motion vectors 620 in a variety of different ways in various embodiments of method 700. For example, a weighted least square method may be utilized. Various factors may be utilized in the weighted least square method. For example, the weighted least square method may be based on a relaxation factor, number of total photon coincidence counts, amplitude of respiration, regularity of respiratory motion, noise, signal to noise ratio, regularity of cycle from the electrocardiogram, or other suitable variables. In step 706, the combined respiratory motion vectors 704 are used to reconstruct the PET cardiac acquisition data to generate a respiratory motion free cardiac image 708.

Figure 8:
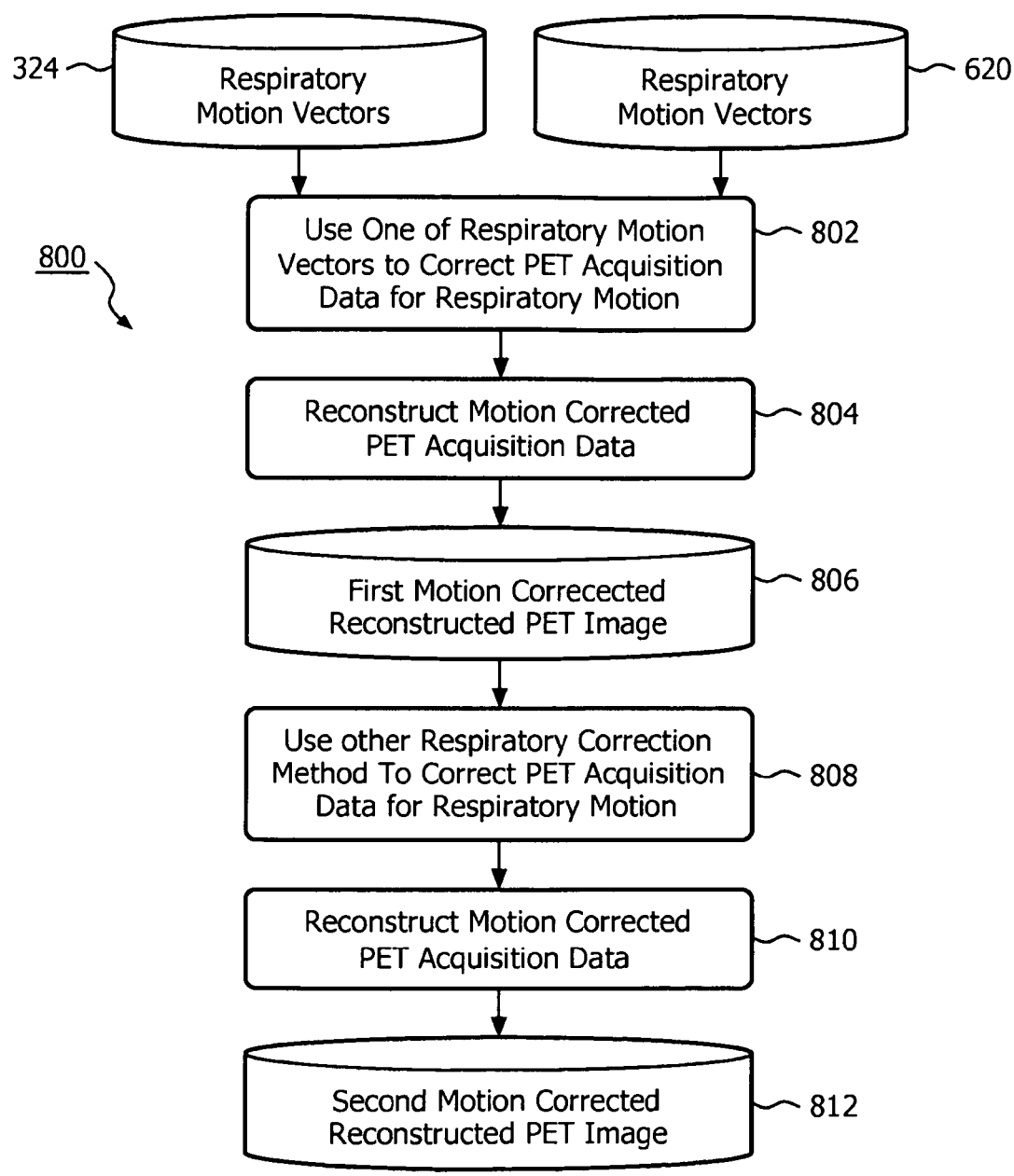
FIG. 8 depicts an exemplary iterative process for combining the results of the methods of FIG. 3 and FIG. 6.

In various additional embodiments, an iterative process may be used to combine the respiratory motion vectors 324, 620. Referring to FIG. 8, an exemplary iterative method 800 for combining the respiratory motion vectors 324, 620 is depicted. According to this method, one of the sets of respiratory motion vectors 324, 620 obtained by method 300 or 600 is utilized by itself to correct for the respiratory motion in step 802. In step 804, once respiratory motion has been accounted for in this manner, the PET acquisition data is reconstructed to obtain a first motion corrected reconstructed PET image 806. In step 808, using the new reconstruction 806, respiratory motion is then estimated using the motion estimation method 300 or 600 that was not previously used in step 802. In step 810, the motion corrected PET acquisition data is reconstructed to obtain a second motion corrected reconstructed PET image 812. The steps of iterative method 800 are then repeated, using either motion correction method 300 or 600 for each iteration of method 800 as necessary to correct for respiratory motion.

Once respiratory motion has been removed from the cardiac PET images, the major portion of the motion left in the cardiac PET image is due to cardiac motion. Following the removal of respiratory motion from the PET acquisition data, cardiac motion can then be estimated and removed. In various embodiments, this method is applied to the whole left ventricle. In various additional embodiments, this method is applied independently to each of the 17 segments of the heart. In various additional embodiments, this method is applied to each pixel of the left ventricle of the heart. Various additional spatial decompositions of the heart could also be utilized in additional embodiments.

As mentioned previously, once respiratory motion has been removed from the cardiac PET images, the major portion of the motion left in the cardiac PET image is due to cardiac motion. If the heart is processed as a whole, the residual motion is the same for the whole heart. If the heart is analyzed as 17 segments, the residual motions are different from segment to segment. However, it should be understood that the granularity of the spatial decomposition of the heart depends on the count density per region.

In various embodiments, the respiratory motion is first estimated, then removed from the original PET cardiac data. Then, the cardiac motion is estimated and removed from the respiratory motion corrected PET cardiac data. In various additional embodiments of the present invention, the estimation and removal of respiratory motion and cardiac motion from the PET data is carried out by an iterative process by simply repeating estimation and removal of the respiratory motion and the estimation and removal of the cardiac motion. In this manner, the cross-contamination of the respiratory motion estimates and cardiac motion estimates will be minimized.

In various embodiments of the present invention, the respiratory and cardiac motion corrections are performed in image space. However, in additional embodiments of the present invention, the respiratory and/or cardiac motion corrections are introduced at the level of the lines of response 112. In such embodiments, the original list mode data is modified using the respiratory and/or cardiac motion estimations and then a reconstruction is performed.

In various embodiments of the present invention, the respiratory motion and cardiac motion are estimated for the entire cardiac region. In additional embodiments, the estimation of respiratory motion and cardiac motion is focused solely on the left ventricle. In yet further additional embodiments, separate estimations are made independently for one or more of each of the 17 segments of the heart. In yet further additional embodiments, the methodology used for estimating respiratory and cardiac motion is applied to each pixel of the left ventricle, or each pixel of another particular region of the heart.

However, it should be understood that inherent limitations reside in the number of photon coincidence counts that are available from the region of the heart being imaged. For example, if a particular region of the heart is too small, then the number of photon coincidence counts available for data computation will not allow for an accurate estimation of the respiratory motion or cardiac motion. The granularity of the spatial decomposition of the heart depends on the photon coincidence count density per region. As discussed previously, while the exemplary methods described are directed to cardiac PET imaging, the disclosed methods also have applicability in other types of PET imaging or with other imaging modalities, such as CT or SPECT. The disclosed methods have particular applicability to imaging modalities that provide data in a list mode format.

The previously described motion characterization and correction methods have a variety of uses and benefits. For example, the methods described herein are helpful in sharpening a gated PET image and improving the reconstruction of the gated PET images. In addition, the motion correction methods described herein may be used to improve a dynamic PET reconstruction.

Figure 9:
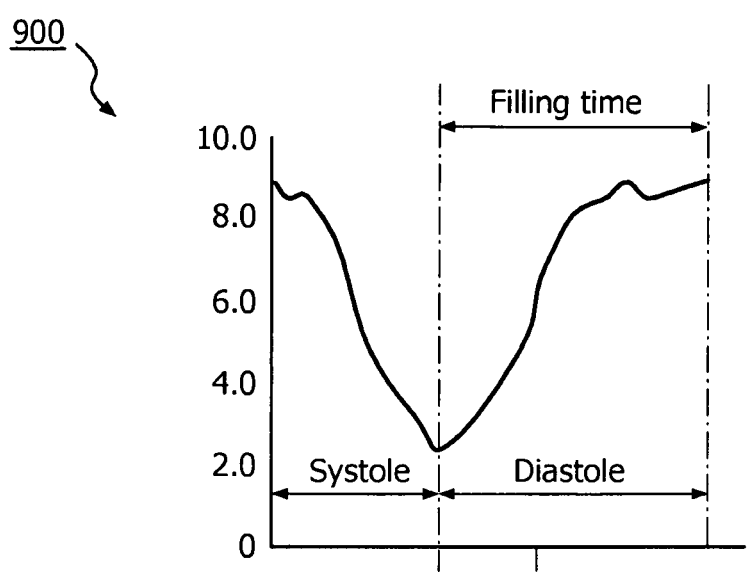
FIG. 9 depicts an exemplary curve representing the volume of blood flow over time.

One additional potential use for the motion correction methods described herein is to determine the ejection fraction of the heart. An exemplary curve 900 representing the volume of blood flow over time is set forth in FIG. 9. The ejection fraction is a commonly recognized measurement of the health of the heart, and it may be calculated as follows. The volume of blood within a ventricle immediately before a contraction is known as the end-diastolic volume. The volume of blood within the ventricle at the end of contraction is known as the end-systolic volume. The difference between the end-diastolic and end-systolic volumes is the stroke volume, or the volume of blood ejected from the ventricle with each beat. The ejection fraction is the fraction of the end-diastolic volume that is ejected with each beat; that is, it is stroke volume (SV) divided by end-diastolic volume (EDV), as follows:

$$\text{Ejection Fraction} = SV/EDV = (EDV - ESV)/EDV.$$

The motion corrections described herein can also be used to obtain improved absolute blood flow measurements or to perform other functions based on underlying PET imaging data.

The aforementioned functions, such as for example, initiating and/or terminating scans, selecting desired scan or reconstruction protocols, manipulating the volumetric data, and the like, can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic, databases or tables shown and described herein preferably reside in or on a computer readable medium. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method of detecting motion occurring during an imaging acquisition with a medical imaging system, comprising the steps of:
   conducting an imaging acquisition of an imaged subject with an imaging system to generate image acquisition data including time of flight data;
   monitoring the time of flight data during the imaging acquisition; and
   analyzing the time of flight data to detect motion of the imaged subject occurring during the imaging acquisition.

2. The method of claim 1, wherein the imaging acquisition is a PET imaging acquisition.

3. The method of claim 2, further comprising comparing the time of flight data to a pre-selected threshold, and providing a warning to an operator of the imaging system when the time of flight data exceeds the pre-selected threshold.

4. The method of claim 1, wherein the image acquisition data is list mode data.

5. The method of claim 1, further comprising the step of converting the time of flight data into a position metric representative of motion of the imaged subject occurring during the imaging acquisition.

6. The method of claim 5, wherein the position metric is a respiratory wave position metric representative of respiratory motion occurring during the imaging acquisition.

7. The method of claim 6, further comprising the step of utilizing the respiratory wave position metric to generate gating signals for respiratory framing of the image acquisition data.

8. The method of claim 5, wherein the position metric is a gross motion position metric representative of gross motion of the imaged subject occurring during the imaging acquisition.

9. The method of claim 8, further comprising comparing the gross motion position metric to a pre-selected threshold, and providing a warning to an operator of the imaging system when the gross motion position metric exceeds the pre-selected threshold.

10. The method of claim 1, further comprising:
    acquiring an electrocardiogram of the imaged subject during the medical imaging acquisition;
    utilizing the electrocardiogram to gate the imaging acquisition data to generate cardiac gated acquisition data;
    dividing the cardiac gated acquisition data into sub-intervals of time to obtain respiratory gated cardiac images;
    determining a center of activity in the respiratory gated cardiac images; and
    comparing the centers of activity in different respiratory gated cardiac images to generate respiratory motion vectors.

11. The method of claim 10, wherein the imaging acquisition data is list mode data.

12. The method of claim 10, further comprising using the respiratory motion vectors to correct the imaging acquisition data and generate a respiratory motion free cardiac image.

13. The method of claim 12, further comprising removing cardiac motion from the respiratory motion free cardiac image.

14. The method of claim 1, further comprising:
    acquiring an electrocardiogram of the imaged subject during the medical imaging acquisition;
    utilizing the electrocardiogram to divide the imaging acquisition data into cardiac cycles;
    determining a center of activity in the cardiac cycles;
    comparing the centers of activity in different cardiac cycles to generate respiratory motion vectors.

15. The method of claim 14, wherein the imaging acquisition data is list mode data.

16. The method of claim 14, further comprising using the respiratory motion vectors to correct the imaging acquisition data and generate a respiratory motion free cardiac image.

17. The method of claim 16, further comprising the step of removing cardiac motion from the respiratory motion free cardiac image.

18. The method of claim 14 further comprising the steps of:
    utilizing the electrocardiogram to divide the imaging acquisition data into cardiac cycles;
    determining a center of activity in the cardiac cycles; and
    comparing the center of activity in different cardiac cycles to generate a second set of respiratory motion vectors.

19. The method of claim 18, further comprising the step of combining the first set of respiratory motion vectors with the second set of respiratory motion vectors to generate a set of combined respiratory motion vectors.

20. The method of claim 19, wherein the first set of respiratory motion vectors is combined with the second set of respiratory motion vectors with a weighted least square method or through an iterative process.

21. The method of claim 19, wherein the method is utilized to determine the ejection fraction of a heart.

22. The method of claim 19, wherein the respiratory motion vectors are determined separately for at least two segments of a heart.

23. The method of claim 19, wherein the respiratory motion vectors are determined separately for each pixel of one segment of a heart.

24. The method of claim 18, further comprising:
    converting the time of flight imaging acquisition data into a respiratory wave position metric representative of respiratory motion occurring during the imaging acquisition; and
    combining at least one of the first set of respiratory motion vectors and the second set of respiratory motion vectors with the respiratory wave position metric to generate a set of combined respiratory motion vectors.

25. A medical imaging system adapted to detect motion occurring during an imaging acquisition of an imaged subject, comprising:
    at least one detector which detects radiation emitted by the imaged subject; and
    a computer readable non-transitory medium including logic comprising:
        conducting the imaging acquisition of the imaged subject to generating image acquisition data including time of flight data;
        monitoring the time of flight data during the imaging acquisition; and
        analyzing the time of flight data to detect motion of the imaged subject occurring during the imaging acquisition.

26. The medical imaging system of claim 25, wherein the imaging acquisition is a PET imaging acquisition.

27. The medical imaging system of claim 25, wherein the medical imaging system is a PET imaging system.

28. The medical imaging system of claim 25, wherein the image acquisition data is in the form of a list mode.

29. The medical imaging system of claim 25, wherein the logic comprises converting the time of flight data into a position metric representative of motion of the imaged subject occurring during the imaging acquisition.

30. The medical imaging system of claim 29, wherein the position metric is a respiratory wave position metric representative of respiratory motion occurring during the imaging acquisition.

31. The medical imaging system of claim 30, wherein the logic further comprises utilizing the respiratory wave position metric to generate gating signals for respiratory framing of the image acquisition data.

32. The medical imaging system of claim 29, wherein the position metric is a gross motion position metric representative of gross motion of the imaged subject occurring during the imaging acquisition.

33. The medical imaging system of claim 32, wherein the logic further comprises comparing the gross motion position metric to a pre-selected threshold, and providing a warning to an operator of the imaging system when the gross motion position metric exceeds the pre-selected threshold.

34. A method of detecting motion occurring during an imaging acquisition with a medical imaging system, comprising the steps of:
   conducting an imaging acquisition of an imaged subject with an imaging system to generate image acquisition data including time of flight data;
   analyzing the time of flight data to detect motion of the imaged subject occurring during the imaging acquisition;
   converting the time of flight data into a position metric representative of motion of the imaged subject occurring during the imaging acquisition, wherein the position metric is a gross motion position metric representative of gross motion of the imaged subject occurring during the imaging acquisition.

35. A medical imaging system adapted to detect motion occurring during an imaging acquisition of an imaged subject, comprising:
   at least one detector which detects radiation emitted by the imaged subject; and
   a computer readable non-transitory medium including logic comprising:
      conducting the imaging acquisition of the imaged subject to generating image acquisition data including time of flight data;
      analyzing the time of flight data to detect motion of the imaged subject occurring during the imaging acquisition; and
      converting the time of flight data into a position metric representative of motion of the imaged subject occurring during the imaging acquisition, wherein the position metric is a gross motion position metric representative of gross motion of the imaged subject occurring during the imaging acquisition.

* * * * *